US006926688B2

(12) United States Patent
Meyer

(10) Patent No.: US 6,926,688 B2
(45) Date of Patent: Aug. 9, 2005

(54) FOREARM SUPPORT BAND WITH DIRECT PRESSURE MONITORING

(76) Inventor: Nicholas Joseph Meyer, 4210 Evergreen La., Plymouth, MN (US) 55441

( * ) Notice: Subject to any disclaimer, the term of this patent is extended or adjusted under 35 U.S.C. 154(b) by 0 days.

(21) Appl. No.: 10/230,248

(22) Filed: Aug. 28, 2002

(65) Prior Publication Data

US 2003/0045826 A1 Mar. 6, 2003

Related U.S. Application Data

(60) Provisional application No. 60/315,585, filed on Aug. 29, 2001, now abandoned.

(51) Int. Cl.$^7$ ................................................ A61F 5/00
(52) U.S. Cl. ............................ 602/62; 602/13; 602/20; 602/60
(58) Field of Search ............................ 602/13, 20, 21, 602/60, 61, 62, 64; 128/878, 879

(56) References Cited

U.S. PATENT DOCUMENTS

| | | | |
|---|---|---|---|
| 2,533,504 A | 12/1950 | Poor | 128/24 |
| 2,823,668 A | 2/1958 | Van Court | 128/87 |
| 3,102,534 A | 9/1963 | Bigliano et al. | 128/2.05 |
| 3,299,882 A | 1/1967 | Masino | 128/2.05 |
| 3,351,055 A | 11/1967 | Gottfried | 128/87 |
| 3,454,010 A | 7/1969 | Lilligren | 128/327 |
| 3,548,819 A | 12/1970 | Davis et al. | 128/82.1 |
| 3,633,567 A | 1/1972 | Sarnoff | 128/2.05 |
| 3,717,145 A | 2/1973 | Berndt et al. | 128/82.1 |
| 3,785,371 A | 1/1974 | Lewis | 128/77 |
| 3,877,426 A | 4/1975 | Nirschl | 128/165 |
| 3,901,225 A | 8/1975 | Sconce | 128/89 |
| 3,970,081 A | 7/1976 | Applegate | 128/95 |
| 3,975,015 A | 8/1976 | Owens et al. | 273/54 |
| 4,014,327 A | 3/1977 | Spiro | 128/165 |
| 4,027,666 A | 6/1977 | Marx | 128/165 |
| 4,030,484 A | 6/1977 | Kuska et al. | 128/2.05 |
| 4,146,021 A | 3/1979 | Brosseau et al. | 128/75 |
| 4,182,318 A | 1/1980 | Beige et al. | 128/77 |
| 4,191,373 A | 3/1980 | Lancellotti | 273/29 |
| 4,210,154 A | 7/1980 | Klein | 128/685 |
| 4,378,009 A | 3/1983 | Rowley et al. | 128/83 |
| 4,476,857 A | 10/1984 | Levine | 128/77 |
| 4,628,918 A | 12/1986 | Johnson, Jr. | 128/90 |
| 4,773,397 A | 9/1988 | Wright et al. | 128/24 |
| 4,862,879 A | 9/1989 | Coombs | 128/87 |
| 4,905,998 A | 3/1990 | Last | 273/29 |
| 4,920,971 A | 5/1990 | Blessinger | 128/679 |
| 4,993,422 A | 2/1991 | Hon et al. | 128/672 |
| 5,152,302 A | 10/1992 | Fareed | 128/878 |
| 5,172,689 A | 12/1992 | Wright | 128/400 |
| 5,245,990 A | 9/1993 | Bertinin | 128/64 |
| 5,295,951 A | 3/1994 | Fareed | 602/62 |
| 5,310,400 A | 5/1994 | Rogers et al. | 602/5 |
| 5,514,081 A * | 5/1996 | Mann | 602/20 |
| 5,865,775 A * | 2/1999 | Peoples et al. | 602/20 |
| 5,954,676 A * | 9/1999 | Kramer, III | 602/6 |
| 5,976,099 A | 11/1999 | Kellogg | 602/23 |
| 6,007,508 A * | 12/1999 | Reinhardt et al. | 602/62 |
| 6,179,800 B1 | 1/2001 | Torrens | 602/21 |
| 6,398,749 B1 * | 6/2002 | Slautterback | 602/62 |
| 6,436,064 B1 * | 8/2002 | Kloecker | 602/13 |
| 6,478,760 B2 * | 11/2002 | Darcey | 602/20 |

FOREIGN PATENT DOCUMENTS

JP          2034143         2/1990

\* cited by examiner

*Primary Examiner*—Henry Bennett
*Assistant Examiner*—Amanda Wieker
(74) *Attorney, Agent, or Firm*—Hoffman, Wasson & Gitler PC

(57) ABSTRACT

The forearm support band with direct pressure monitoring provides the ability for patients to optimize treatment of medial or lateral epicondylitis (golfer's elbow or tennis elbow, respectively) with the use of optimal pressure application. Unlike previous forearm support bands, this band allows patients to directly read the pressure of application and appropriately adjust the band's tightness. This results in the correct amount of pressure to the forearm musculature, thereby minimizing risks and gaining optimal therapeutic benefits.

2 Claims, 5 Drawing Sheets

FOREARM SUPPORT BAND WITH DIRECT PRESSURE MONITORING

CROSS-REFERENCE TO RELATED APPLICATIONS

This appln. claims benefit of 60/315,585 filed Aug. 29, 2001 now abandoned.

STATEMENT REGARDING FEDERALLY SPONSORED RESEARCH OR DEVELOPMENT

Not Applicable

BACKGROUND OF THE INVENTION

This invention relates to the use of a compressive band for the relief of either medial or lateral epicondylitis ("golfer's elbow" or "tennis elbow," respectively), but may be extrapolated to other forms of tendonitis. Specifically, this invention optimizes the application pressure of the compressive band through direct measurement of said pressure, allowing the user to apply the band to the most effective pressure and avoid ineffective (low) pressure or excessive (high) pressure.

The forearm support band (also known as the tennis elbow brace, forearm counterforce brace, or tennis elbow band) is currently produced in a variety of designs. At its basis, the forearm support band (hereafter FSB) is designed to apply compression to the forearm to alleviate symptoms associated with lateral epicondylitis or tennis elbow. As well, the FSB may be utilized for symptoms associated with medial epicondylitis or golfer's elbow. This goal of compression is achieved through application of a band designed of varying materials, often fastened with hook and loop material, about the proximal forearm. This creates compression of the forearm during activities that aggravate the symptoms associated with tennis or golfer's elbow. While the mechanism of action of the FSB is not completely known, nor has its efficacy been proven, anecdotal evidence exists as to the clinical effectiveness of the FSB in the treatment of tennis and golfer's elbow.

Two general designs exist for the FSB. One involves a simple circumferential band that applies equal pressure circumferentially around the forearm; the other applies eccentric pressure over the area of pathology (if applied correctly) through an air pillow or bladder.

One current design incorporates an air bladder contained in a pocket of inelastic material on its outer surface (away from the skin) and a semi-pliable material against the skin. By applying the air bladder over the muscle bellies of interest (the wrist extensors for tennis elbow and the wrist flexors for golfer's elbow), this allows increased compression localized to the area of pathology.

Regardless of the type or design of the FSB used, no band currently in production allows for the careful regulation or monitoring of pressure either during application or activity. The band is applied to a firm but comfortable pressure determined by the user. No defined or objective goal pressure is sought. In fact, the scientific literature is littered with references regarding the application of the forearm support band, none of which define a goal pressure. For example, to describe the tension at which the forearm band has been applied, authors in varying reports describe "adjusted to a comfortable degree with the muscles relaxed so that maximum contraction of the wrist and finger flexors and extensors is inhibited by the band," (Froimson, A. I.: Treatment of tennis elbow with forearm support band. *The Journal of Bone and Joint Surgery*, 53(A): 183–184, 1971) "secure . . . so that a subject felt comfortable when relaxed but noticed tension when contracting his/her forearm muscles," (Wadsworth, C. T.; Nielsen, D. H.; Burns, L. T.; Krull, J. D.; and Thompson, C. G.: Effect of the counterforce armband on wrist extension and grip strength and pain in subjects with tennis elbow. *The Journal of Orthopaedic and Sports Physical Therapy*, 11: 192–197, 1989) "wrapped snugly about the bulkiest portion of the upper forearm," (Priest, J. D.: Tennis elbow: the syndrome and a study of average players. *Minnesota Medicine*, 59: 367–371, 1976) and "snugly without pinching the skin." (Snyder-Mackler, L., and Epler, M.: Effect of standard and Aircast tennis elbow bands on integrated electromyography of forearm extensor musculature proximal to the bands. *The American Journal of Sports Medicine*, 17: 278–281, 1989) Obviously, much discrepancy and little objective data exist regarding the optimal pressure of application. However, a recent cadaveric and clinical study performed by the author of this patent (NJM) confirmed that a pressure-dependent effect exists which relies on the pressure of the FSB (higher band pressures decrease overload at the area of pathology). As well, the pressure increases significantly from a low pressure at rest to a relatively high pressure during activity and muscle contraction, which was dependent on the pressure of application. These data suggest that a minimum application pressure of 30–50 mmHg may optimize the principle effect described below. If the support band is to work with a compressive mechanism, its effect will be dependent on the pressure of application and pressure during activity. The basic principle (hereafter referred to as the Principle) is as follows: Pressure must be maximized during activity to achieve optimal effect, but resting pressure must be low enough to minimize the risk of complications related to prolonged, continuous pressure. This is achieved through application of the FSB to a known pressure (as directly monitored on the band), resulting in a predictable pressure increase during activity.

The basic design of the air pillow FSB (U.S. Pat. No. 4,628,918) consisting of an air bladder over the extensor wad appears sound. The flaw in this design exists in the lack of standardization by which patients apply the band. However, the addition of a pressure monitor, either in the form of simple dial or linear pressure monitor built into the air bladder, would allow the user to apply the FSB to a desired goal pressure to achieve the aforementioned Principle effect. In our study, we found that patients familiar with the use of the FSB for treatment of tennis elbow were applying the band to pressures ranging from 20 to 100 mmHg. This is a wide range of application pressures rendering the FSB ineffective at the lower pressures and dangerous at the higher pressures. As well, this pressure monitor could be added to the simple circumferencial design or any other FSB design and need not be restricted to the air bladder design. The spirit of this patent involves the ability to measure the pressure of the FSB during rest and activity, with the goal of achieving the FSB's maximal effect through observation of the aforementioned Principle effect through a controlled, known application pressure.

Another related prior art (U.S. Pat. No. 5,310,400—Therapeutic bandage) envisions a bandage with "an internal air bladder selectively inflated to provide compression to the injury." In reality, this effect is no different than that claimed in U.S. Pat. No. 4,628,918 (referenced above) as the user can selectively provide different levels of compression by applying the band tighter or looser. This prior art suggests the user can adjust the pressure, but makes no claim to achieving an optimal pressure that should be regulated or monitored. Thus, the flaw in this design also rests on the lack of monitoring the application pressure. Our invention allows the user to apply (and adjust) the band to a known, optimal pressure, and to avoid overtightening (excessive pressure) or applying too loosely (low pressure).

BRIEF SUMMARY OF THE INVENTION

This invention involves a direct pressure monitor to allow the forearm support band to be applied to an optimal pressure. This allows the patient to apply the band to a known and ideal pressure, thereby optimizing the effect and minimizing the potential risks associated with the current forearm support band designs. As referenced above in the BACKGROUND OF THE INVENTION, the previous art does not monitor the application pressures, placing the patient at risk of ineffective or excessive compression.

This inventive pressure monitor consists of a monitor directly inside the FSB to give the patient direct feedback as to the application pressure. No claim is made as to an improvement in the current FSB materials other than the air bladder and monitor. The preferred embodiment of the monitor consists of a minimally-compressible air bladder, with the inner air in continuity with a more elastic material with will expand and contract with pressure. This expansion and contraction will take place inside a calibrated hollow cylinder, displacing a plunger against a spring which indicates the pressure exerted within the air bladder. This may, however, take the form of a dial pressure gauge, electric pressure gauges, and sound, vibratory, or visual alerts as technology progresses in the form of inexpensive pressure measurement.

DETAILED DESCRIPTION OF THE INVENTION

The Pressure Monitor will consist of a minimally-compressible air bladder measuring approximately 5 centimeters width by 5 centimeters length by 15 millimeters height. The bladder will have an inherent pressure to maintain its resting shape. This air bladder will be constructed of a minimally-compressible material (such as a semi-compressible plastic) and contain within its structure a pressure monitor. The monitor will consist of a hollow rigid plastic cylinder in continuity with the air bladder itself on one end, and open to the outside atmospheric pressure on the other end. At the point at which the cylinder meets the air bladder, a pliable, elastic material (similar to a balloon) will seal the air bladder and protrude into the cylinder. This will be doubled on itself within the cylinder at rest. This "balloon" will then be in contact with a low-friction plunger, directed away from the balloon and into the cylinder. The plunger, in turn, will be in contact with a spring, which will provide the appropriate resistance to measure the pressure exerted upon the system. This monitor will be calibrated for the inherent pressure and marked for pressures from 20–60 mmHg (these markings may be increased as needed to include measurements for activity pressures up to 150 mmHg). This monitor or gauge will be visible through a window in the outer surface of the support band. A green or other colored mark may indicate the goal pressure of application (likely 30–50 mmHg). The patient will apply the band to a goal pressure (likely 30–50 mmHg) as directly measured during application, and be alerted to pressure which may be too high or too low by the pressure monitor. Thus, the user can make the appropriate adjustments to the FSB to correct the excessive or insufficient pressure. The spirit of the previously described band (U.S. Pat. No. 4,628,918) currently produced may be maintained for the housing of the pressure monitor. The FSB will be applied through the typical hook and loop material mechanism and fastened when the desired pressure is achieved. A secondary fastening element, such as additional straps or dial devices, or a pump mechanism with one-way valve incorporated into the air bladder (U.S. Pat. No. 5,310,400 —prior art) may also be added to "fine tune" the application pressure. Continuous monitoring of the resting pressure of application will allow the user to periodically adjust the tension and pressure of the FSB as loosening, tightening, and/or shifting of the FSB may result in a change in the resting pressure.

Figure 1A:
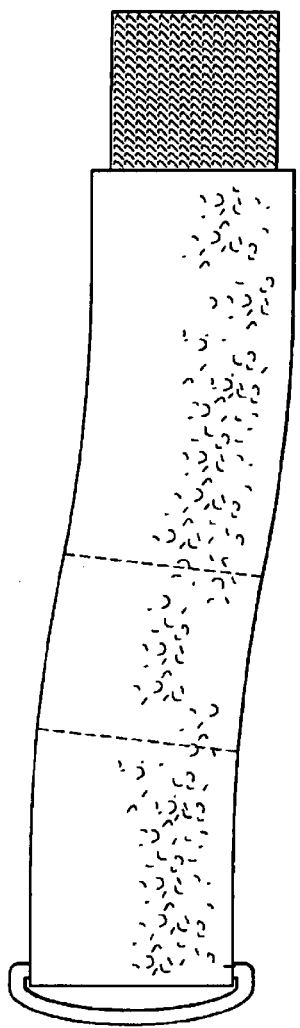
FIGS. 1A–1D: Four drawings showing the forearm support band laid flat prior to insertion of the air bladder/pressure monitor, the air bladder/pressure monitor outside of the band, with the air bladder/pressure monitor in place, and as applied to a theoretical forearm.
Figure 1C:
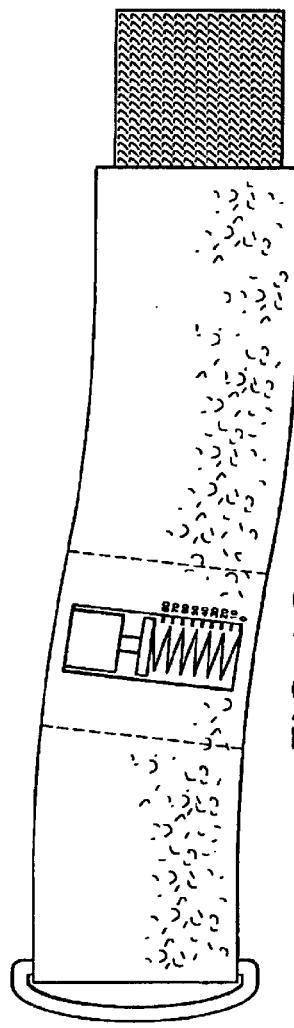
Figure 1B:
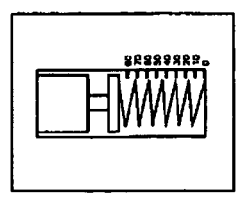
Figure 1D:
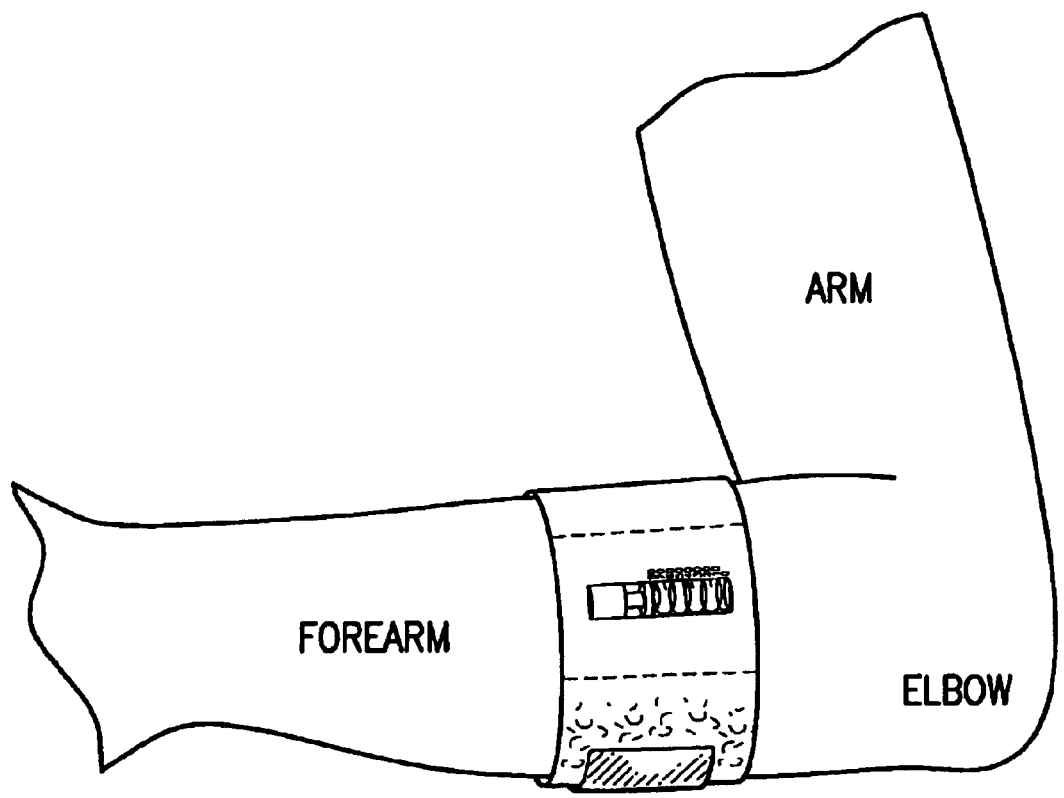
Figure 2:
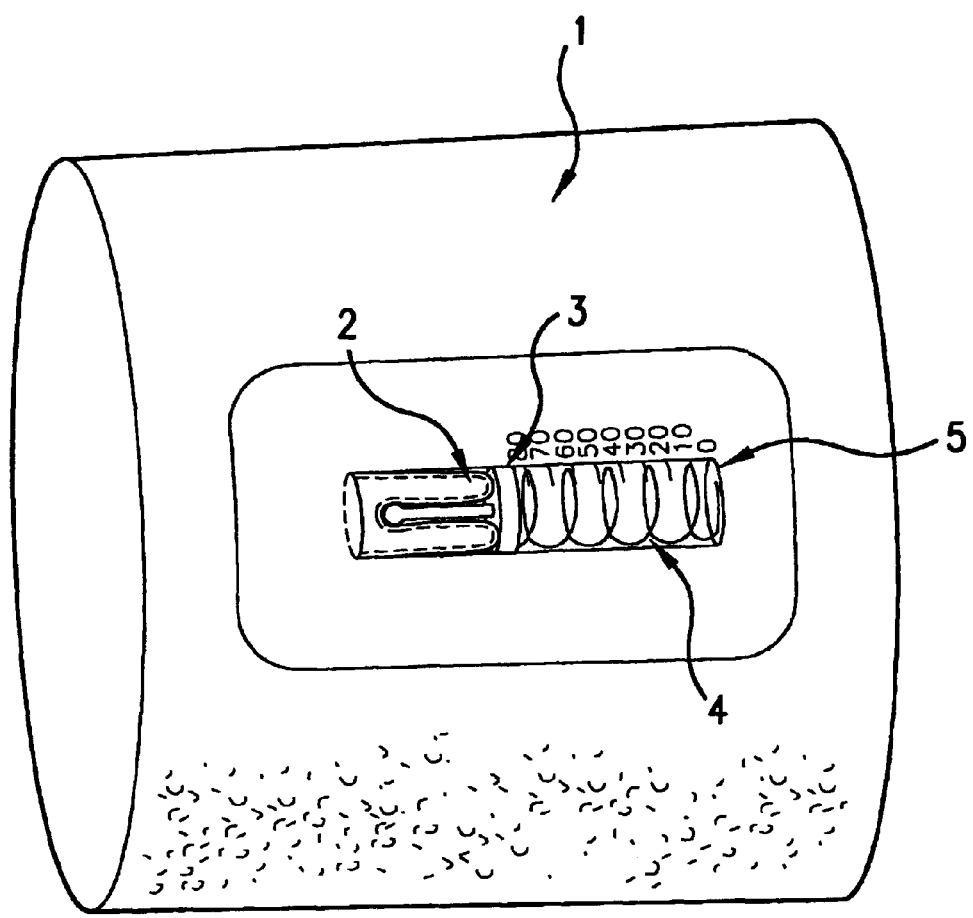
FIG. 2: Top-down close-up view of the air bladder/pressure monitor device
Figure 3:
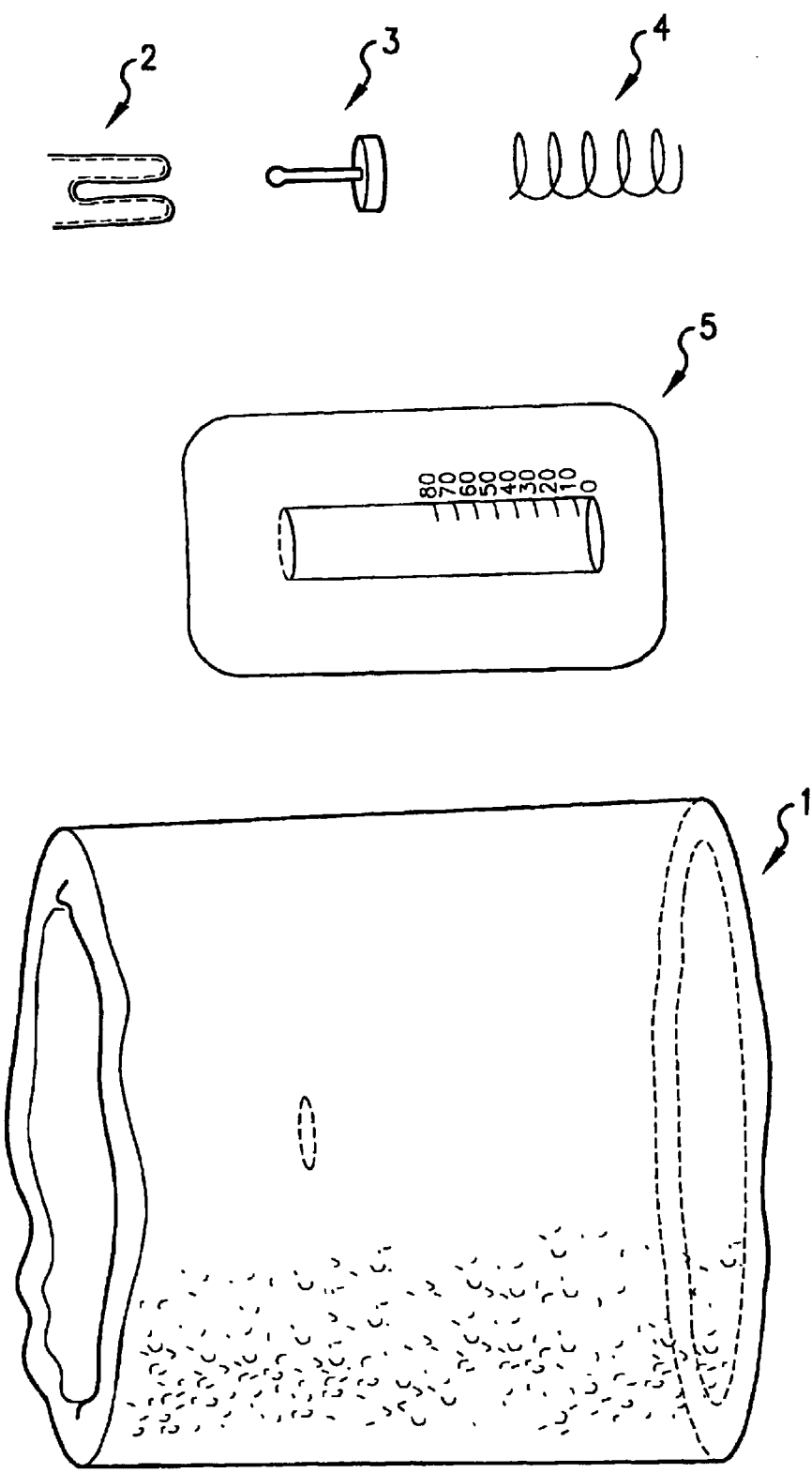
FIG. 3: Detail of the parts involved in the air bladder/pressure monitor device
Figure 4:
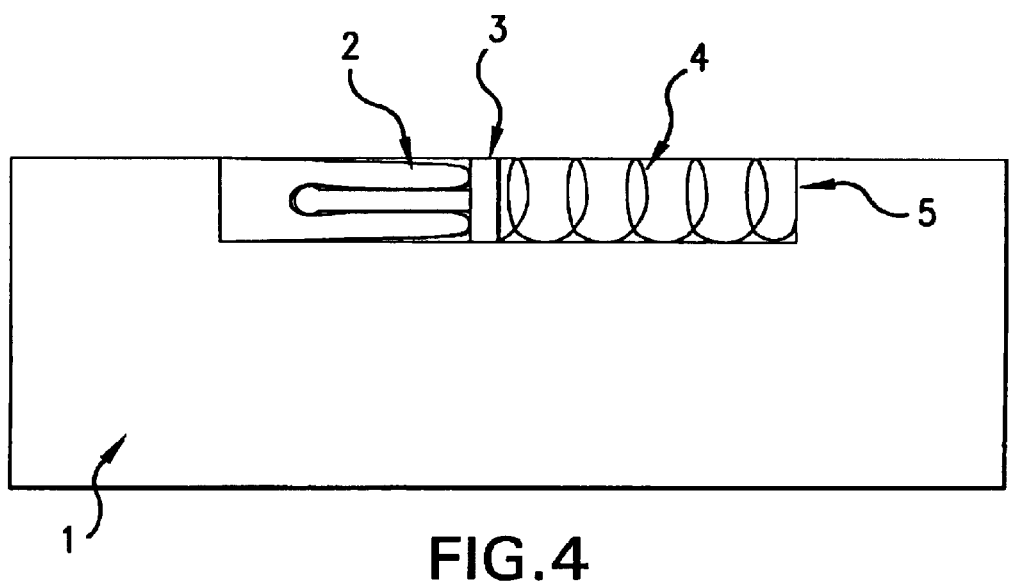
FIG. 4: Cross-section of the preferred air bladder/pressure monitor device

FIGS. 2–4 show the air bladder/pressure monitor in its preferred embodiment. The air bladder 1 in continuity with the flexible, expandable balloon portion of the system 2; which is housed in a rigid, clear plastic cyclinder 5. As the balloon expands with increased pressure, this displaces the plunger 3 within the plastic cylinder 5 against the spring 4. Pressure is read off of the calibrations on the plastic cylinder 5 based on the level of the plunger head 3. The plastic cylinder 5 will be open to the outside atmosphere if resistance is provided by the spring, or closed if the resistance is to be provided by pressure within the cylinder.

What I claim as my invention is:

1. A device to treat epicondylitis, comprising
    a support band, said support band having an outer surface and a retainer for securing said support band to an arm,
    a bladder inside said support band,
    a pressure monitor in communication with said bladder for indicating the pressure within said bladder, said pressure monitor forming part of the support band outer surface wherein
    said pressure monitor comprises a cylinder having a first end in communication with said bladder and a second end in communication with the atmosphere,
    a plunger movable within said cylinder,
    a spring located between said cylinder second end and said plunger.

2. The device of claim 1, wherein said bladder is smaller than said support band.

* * * * *